United States Patent [19]

Corsi et al.

[11] Patent Number: 5,559,241
[45] Date of Patent: Sep. 24, 1996

[54] PROCESS FOR THE PREPARATION OF STERILE AMOXYCILLIN SODIUM SALT

[75] Inventors: Giordano B. Corsi, Genzano; Alberto Brandt, Rome; Loredana Cecchetelli, Castelgandolfo, all of Italy

[73] Assignee: Instituto Biochimico Italiano Giovanni Lorenzini S.p.A., Milan, Italy

[21] Appl. No.: 528,546

[22] Filed: Sep. 15, 1995

Related U.S. Application Data

[63] Continuation of Ser. No. 130,969, Oct. 4, 1993, abandoned.

[30] Foreign Application Priority Data

Oct. 5, 1992 [IT] Italy ................................. MI92A2296

[51] Int. Cl.$^6$ ................................................. C07D 277/60
[52] U.S. Cl. ........................................... 548/178; 514/197
[58] Field of Search ..................................... 514/368, 410, 514/197; 548/178

[56] References Cited

U.S. PATENT DOCUMENTS

| | | | |
|---|---|---|---|
| 3,192,198 | 6/1965 | Nayler et al. | 260/239.1 |
| 4,387,051 | 7/1983 | Corbett et al. | 260/245.2 T |

FOREIGN PATENT DOCUMENTS 0131147  1/1985  European Pat. Off.

*Primary Examiner*—Brian Burn
*Attorney, Agent, or Firm*—George P. Hoare, Jr.; Rogers & Wells

[57] ABSTRACT

A process for the preparation of sterile sodium amoxycillin characterized by the fact that a solution of amoxycillin trihydrate in a mixture of methyl alcohol and a lower $C_2$–$C_5$ alcohol is reacted in a sterile ambient, optionally in the presence of a suitable amine, with a solution of a suitable salifying agent selected from the group consisting of an alcoholate or carboxylate of sodium in methyl acetate followed by separation of the precipitate is described.

6 Claims, No Drawings

PROCESS FOR THE PREPARATION OF STERILE AMOXYCILLIN SODIUM SALT

This application is a continuation of Ser. No. 08/130,969, filed Oct. 4, 1993, now abandoned.

The present invention relates to a method for the production of B-lactam antibiotics and in particular to the method for the production of the sodium salt of the penicillin antibiotic amoxycillin in sterile form. Amoxycillin is a well known semi-synthetic penicillin of wide clinical use. For parenteral administration it is employed in the form of its sodium salt. Among all the sodium salts of the penicillins which are mostly employed, it is likely that the sodium salt of amoxycillin is the one which requires the most caution as far as its industrial production is concerned. Actually amoxycillin, more than the other penicillins, tends to form polymeric degradation products which start from the opening of the β-lactam ring. Apart from amoxycilloic acid, among these degradation products have also been identified dimers, trimers and diketopiperazine derivatives (J. Chromat. 321, 441, 1985) to which are partly due some allergic phenomena which sometimes appear during the administration of penicillin, in particular when the amoxycillin sodium salt is parenterally administered. At present, several methods for amoxycillin production are known which may be roughly classified into two general categories: the first ones contemplate the separation of the amoxycillin sodium salt from aqueous solutions according to methods such as spray-dry or freeze-drying, the second ones contemplate the precipitation from non-aqueous solvents. In some cases an intermediate precipitation of the sodium salt in the form of solvate from suitable solvents, often of amidic nature, is effected. However, upon examination of the products in commerce, it can easily be observed that, in the first case, a product is obtained characterized by a high content of polymeric products (ca. 5–6% at the production) and a high water content value (2–4%) which, to some extent, negatively influence the stability of the product over a length of time. In the second case, the product, besides the substantive content in polymeric products, keeps a certain amount of residual solvents (2–3%) even after drying and also, normally, a certain amount of salifying agent, which lessens the quality of the product itself.

EP-A-131147, which relates to the production of crystalline sodium amoxycillin starting from a corresponding solvate by removing the solvating solvent therefrom, describes among other methods a method which involves salifying an amoxycillin trihydrate suspension in methyl acetate with a sodium alcoholate or carboxylate solution in methanol. After filtration of the solution obtained, which contains in an unstable equilibrium the solvate of sodium amoxycillin, a further addition of the solvating agent methyl acetate determines the precipitation of the solvate from which, by removing the methyl acetate solvating solvent, the crystalline sodium amoxycillin is obtained. Even if it supplies a product having satisfactory characteristics, said method has the particularly serious inconvenience of presenting, on an industrial scale, possible precipitations at the phase of the sterilizing filtration, with the consequent obstruction of the filter, due to the instability of the solution containing the sodium amoxycillin solvate. It has now been found that the inconveniences of the prior art, in particular concerning the realization on industrial scale of the above-mentioned process described in EP-A- 131147, may be overcome by the process of the present invention, according to which the salification of the amoxycillin trihydrate is performed in a sterile ambient by reacting a solution of the same, optionally in the presence of a suitable base, in a mixture of methanol and a $C_2$–$C_5$ lower alcohol with a solution of the salifying agent in methyl acetate. Preferably, the $C_2$–$C_5$ alcohol is isopropanol, and the ratios of methanol/isopropanol are in the range of 70:30–30:70, preferably in the range of 60:40–50:50.

The process of the present invention makes it possible to obtain a sterile product by precipitation from a non-aqueous solvent which is characterized by an extremely low content of degradation products, particularly of polymeric products (at an average of ca. 1%), by an extremely low content of residual solvents, water inclusive, and further, by a very low content of the residual precipitating agent (0.5%).

In practice, the salification reaction of amoxycillin according to the process of the invention consists of a double exchange reaction in a sterile ambient between the salt of amoxycillin e.g. triethylamine salt, in the alcohol mixture and the salifying agent, e.g. sodium 2-ethylhexanoate, in methyl acetate. The amoxycillin sodium salt is formed in an ambient where it is insoluble and from which it separates by precipitation.

An advantage of the process of the present invention of particular relevance when concerning its industrial application is represented by the fact that the amoxycillin trihydrate solution, in the mixture formed by methanol and a $C_2$–$C_5$ alcohol being stable, can be sterilely filtered without any risk of having undesired precipitations.

A further advantage of the process according to the present invention is that the sodium salt of amoxycillin is obtained directly in a sterile ambient, which represents an event of great importance in the industrial realization of the process itself.

Further advantages of the process of the invention are represented by the favorable rheological characteristics of the powder obtained, with subsequent advantages in the preparation of the pharmaceutical forms and by the absence of environmental and toxicological problems connected to the use of chlorinated solvents.

According to a preferred embodiment of the process of the invention, the amoxycillin trihydrate is dissolved in a mixture of alcoholic solvents containing a suitable organic base and then filtering the same in a solution of sodium alcoholate or carboxylate in methyl acetate previously sterilely filtered. When the additions are over, the solution is cooled to a temperature between 20° and −20° C. and a suitable amount of methyl acetate is optionally added in order to complete the product precipitation. The sterile sodium salt which precipitates is filtered, washed with the same solvent or a suitable mixture of solvents, and dried.

The following Examples further illustrate the invention.

EXAMPLE 1

| REAGENTS | |
|---|---|
| Amoxycillin.$3H_2O$ | g 70 (0.167 mole) |
| Methanol | ml 215 |
| Isopropanol | ml 160 |
| Triethylamine | ml 50 |
| Sodium 2-ethylhexanoate | g 50 (0.270 mole) |
| Methyl acetate | ml 500 + 1,700 + 500 |

In a flask, provided with a mixer and a loading-funnel, sodium 2-ethylhexanoate is dissolved in a mixture consisting of 500 ml methyl acetate and 30 ml methanol and it is cooled to 20° C. At the same time, in an Erlenmeyer flask, amoxycillin trihydrate is dissolved in a mixture of 185 ml methanol, 160 ml isopropanol and 50 ml triethylamine and then cooled to 10° C. The solution is filtered and, through a loading-funnel, is added to the previously prepared solution contained in the flask, over a period of 10 minutes under fast stirring. During the additions about 1 g of seed is added and then a further 1,700 ml of methyl acetate. It is left for 2 hours under stirring at 0° C. It is filtered on Buncker and washed again suspending the product in 500 ml methyl acetate. After drying in a vacuum oven for a few hours a product weighing 56 g (ponderal yield 80%) is obtained.

Potentiometric titre expressed as anhydrous acid on anhydrous: 89,90%. KF 0.12% and residual solvents determined by GC: 0.46% Polymeric products determined by HPLC: 1.33% IR 3280; 1170; 1690; 1595 cm$^{-1}$ A sample of this product just filtered on Buncker is washed again with methylene chloride. From the GC analysis of the sample not dried, according to the "head space" technique, it was observed that the content in methyl acetate had dropped to a value of less than 3%.

A further sample after being washed with methyl acetate was left in the air in an open container at room temperature and it was observed that the product was extremely non-hygroscopic and that after some hours the methyl acetate content had dropped to a value of less than 6%.

EXAMPLE 2

| REAGENTS | | |
|---|---|---|
| Amoxycillin.3H$_2$O | kg | 100 (238.4 mole) |
| Methanol | l | 304 |
| Isopropanol | l | 226 |
| Triethylamine | l | 71 (51.6 kg, 510 mole) |
| Sodium 2-ethylhexanoate | kg | 64 (385.5 mole) |
| Methyl acetate | l | 2,650 |
| Washing: Methyl acetate | l | 600 |

2-Ethylacetate is dissolved in 400 l methyl acetate and 28 l methanol, then the solution obtained is filtered in the reactor in a sterile ambient. After that 30 l methyl acetate are filtered for washing the lines and the temperature of the solution is brought to 17° C. The external reactor is filled with 240 l methanol, 205 l isopropanol and 71 l triethylamine, then with amoxycillin trihydrate and it is stirred until complete dissolution and cooled to 5° C. Thereto 2 kg celite are added and it is filtered maintaining the solution at 5° C. This solution is filtered through a bell-shaped filter, then through sterilizing pre-filters and finally through sterilizing filters, under stirring, inside the methyl acetate solution previously prepared. The lines are washed again with a solution of 36 l methanol and 21 l isopropanol. When the additions are over the temperature should be about 12°–14° C. Then 1 kg of seed is added, after which it is checked that the salt precipitation starts, and the stirring speed is reduced. The residual of methyl acetate is filtered and the temperature maintained at 12°–14° C. during the additions. It is cooled with brine to 0° C. maintaining this temperature under stirring for about 90 minutes, then it is filtered without pressing the product and the washing is carried out by re-suspending the product itself. The mother waters are completely removed by filtration and the product is dried at 65° C. overnight.

74.15 kg of the product are obtained (molar yield 80.3%). Potentiometric titre 96.18% corresponding to 90.75 as anhydrous acid on anhydrous. Oligomers 1.57% KF 0.59% total solvents 0.58% The IR spectrum was identical to the one of Example 1.

EXAMPLE 3

| REAGENTS | | |
|---|---|---|
| Amoxycillin.3H$_2$O | kg | 70 (167 mole) |
| Methanol | l | 215 |
| Isopropanol | l | 160 |
| Triethylamine | l | 50 (36.35 kg, 359 mole) |
| Sodium 2-ethylhexanoate | kg | 45 (271 mole) |
| Methyl acetate | l | 1,850 |
| Washing: Methyl acetate | l | 1,200 |

2-Ethylhexanoate is dissolved in 280 l of methyl acetate and 20 l methanol, the solution obtained is filtered in a reactor in a sterile ambient. Then 20 l methyl acetate are filtered for the washing of the lines and the temperature of the solution is brought to 20° C.

The external reactor is filled with methanol, isopropanol, triethylamine and then amoxycillin trihydrate. It is stirred until complete dissolution and cooled to 5° C.

Such solution is filtered through a bell-shaped funnel, then through sterilizing pre-filters and finally through sterilizing filters, under stirring, in the methyl acetate solution previously prepared. The lines are washed again with a solution of 25 l methanol and 15 l isopropanol. After the additions, the temperature should be about 15° C. To it is added 1 kg of seed, after which it is checked that the salt precipitation starts, and then the stirring speed is reduced. The remaining methyl acetate is filtered. In the course of the additions the temperature should always be constant. It is cooled with brine to 0° C. and it is left under stirring at this temperature for about 90 minutes. Then it is filtered and the washing is performed by bringing the product in suspension.

It is filtered by eliminating at best all the residual solvent, then it is dried at 65° C. overnight. A product of 52.1 kg (74.43% ponderal yield, 80.6 molecular yield) is obtained. Mercurymetric titre 96.6% equivalent to 91.12 in amoxycillin as acid on anhydrous. Degradation products 1.41%. KF 0.61% total solvents 0.67%

EXAMPLE 4

| REAGENTS | | |
|---|---|---|
| Amoxycillin.3H$_2$O | kg | 70 |
| Methanol | l | 190 + 25 |
| Isopropanol | l | 145 + 15 |
| Triethylamine | l | 50 |
| Sodium 2-ethylhexanoate | kg | 45 |
| Methyl acetate | l | 1,850 |
| Washing: Methyl acetate | l | 225 + 225 |

2-Ethyl hexanoate is dissolved in methyl acetate and it is filtered sterilely in the internal reactor in the sterile area. In a reactor external to the sterile area are loaded 190 l methanol, 145 l isopropanol and 50 l triethylamine. Stirring is started and amoxycillin trihydrate is added thereto. When the solution is completely clear, it is cooled to 5° C.

To the 2-ethyl hexanoate solution, seed is added, and after that, the amoxycillin solution previously filtered sterilely.

The additions should be done slowly until the appearance of the first crystals, after which the procedure can be faster (altogether 25 minutes). The lines are washed again with methanol (25 liters) and isopropanol (25 liters). After 90 minutes at 0° C., it is filtered and washed twice with methyl acetate. After drying for 4 hours at 65° C., 54.45 kg of product (ponderal yield 77.8%, 84.2 molecular) were obtained. Mercurymetric titre 95.65% on anhydrous equivalent to 90.25 as acid on anhydrous. Degradation products 1.65%. KF 0.70% total residual solvents 0.59%

EXAMPLE 5

| REAGENTS | | |
| --- | --- | --- |
| Amoxycillin .3H$_2$O | kg | 70 (167 mole) |
| Methanol | l | 225 |
| n-propanol | l | 180 |
| Triethylamine | l | 50 (36.35 kg, 359 mole) |
| Sodium 2-ethylhexanoate | kg | 45 (271 mole) |
| Methyl acetate | l | 1,850 |
| Washing: | | |
| Methyl acetate | l | 800 |

Sodium 2-ethylhexanoate is dissolved in 1,850 l of methyl acetate. The solution obtained is filtered in the reactor in sterile ambient. Then 20 l of methyl acetate is filtered for washing the lines and the temperature of the solution is brought to 20° C.

In the external reactor methanol, n-propanol, triethylamine and then amoxycillin trihydrate are loaded, and it is stirred until complete dissolution and cooled to 5° C. Such solution is filtered through a bell-shaped funnel, through sterilizing pre-filters, then through sterilizing filters inside, under stirring, the methyl acetate solution previously prepared. The lines are washed again with a solution of 25 l methanol and 15 l n-propanol. At the end of the additions, the temperature should be about 15° C. To the solution is added 1 kg seed, after which it is checked that the salt starts precipitating. Then the stirring speed is reduced.

It is cooled with brine to 0° C. and left under stirring at this temperature for about 90 minutes. Then it is filtered and washed by bringing the product in suspension.

It is filtered removing at best the residual solvent, then it is dried at 65° C. overnight. 53.1 kilograms of product, ponderal yield 75.8%, are obtained. Mercurymetric titre 96.6% on anhydrous equivalent to 91.12 in amoxycillinic acid on anhydrous. Degradation products 1.51%. KF 0,61% total solvents 0.67%

What we claim is:

1. A process for the preparation of sterile sodium amoxycillin comprising reacting a stable solution of amoxycillin trihydrate in a mixture of methyl alcohol and a lower $C_2C_5$ alcohol under sterile conditions with a solution of a suitable salifying agent selected from the group consisting of an alcoholate and carboxylate of sodium in methyl acetate, and separating the resulting precipitate.

2. The process of claim 1, wherein the lower $C_2C_5$ alcohol is isopropanol.

3. The process of claim 1, wherein the reacting step is carried out in the presence of a suitable amine.

4. The process of claim 3, wherein the suitable amine is selected from the group consisting of triethylamine and diethylamine.

5. The process of claim 1, wherein the salifying agent is sodium 2-ethyl hexanoate.

6. The process of claim 3, wherein the solution of amoxycillin trihydrate and the suitable amine in the mixture of methanol and lower $C_2C_5$ alcohol undergoes a sterile filtration before being added to the solution of the salifying agent in methyl acetate.

* * * * *

UNITED STATES PATENT AND TRADEMARK OFFICE
CERTIFICATE OF CORRECTION

PATENT NO. : 5,559,241
DATED : September 24, 1996
INVENTOR(S) : Giordano B. Corsi, Alberto Brandt, Lordeana Cecchetelli It is certified that error appears in the above-indentified patent and that said Letters Patent is hereby corrected as shown below:

Title page, item [73], should read --

Assignee: Istituto Biochimico Italiano Giovanni Lorenzini S.p.A., Milan, Italy

Signed and Sealed this

Twenty-sixth Day of August, 1997

Attest:

BRUCE LEHMAN

Attesting Officer     Commissioner of Patents and Trademarks